US009403012B2

(12) United States Patent
Henry et al.

(10) Patent No.: US 9,403,012 B2
(45) Date of Patent: Aug. 2, 2016

(54) ACTIVE IMPLANTABLE MEDICAL DEVICE WITH AUTOMATIC OPTIMIZATION OF THE CONFIGURATION OF A MULTI-ELECTRODE STIMULATION LEAD

(71) Applicants: SORIN CRM SAS, Clamart (FR); INRIA—Institut National de Recherche en Informatique et en Automatique, Le Chesnay (FR)

(72) Inventors: Christine Henry, Paris (FR); Laure Laporte-Duchemin, Morangis (FR); David Andreu, Montarnaud (FR); Christine Azevedo-Coste, Montbazin (FR); David Guiraud, Montpellier (FR); Pawel Maciejasz, Montpellier (FR); Olivier Rossel, Montpellier (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 14/713,361

(22) Filed: May 15, 2015

(65) Prior Publication Data

US 2015/0328464 A1  Nov. 19, 2015

(30) Foreign Application Priority Data

May 19, 2014  (FR) ..................... 14 54450

(51) Int. Cl.
*A61N 1/00* (2006.01)
*A61N 1/36* (2006.01)
*A61N 1/05* (2006.01)

(52) U.S. Cl.
CPC ........ *A61N 1/36139* (2013.01); *A61N 1/36053* (2013.01); *A61N 1/36057* (2013.01);

(Continued)

(58) Field of Classification Search
CPC ............ A61N 1/0551; A61N 1/36053; A61N 1/36057; A61N 1/36114; A61N 1/36125; A61N 1/36139; A61N 1/36185
See application file for complete search history.

(56) References Cited

U.S. PATENT DOCUMENTS 7,483,747 B2    1/2009  Gliner et al.
2011/0208271 A1 *  8/2011  Dobak ........................... 607/62

(Continued)

FOREIGN PATENT DOCUMENTS

WO    WO-03/099377      12/2003
WO    WO-2004/103455   12/2004

(Continued)

OTHER PUBLICATIONS

Ordelman et al., Selectivity for Specific Cardiovascular Effects of Vagal Nerve Stimulation With a Multi-Contact Electrode Cuff, IEEE Transactions on Neural Systems and Rehabilitation Engineering, vol. 21, No. 1, Jan. 2013, 5 pages.

(Continued)

*Primary Examiner* — George Manuel
(74) *Attorney, Agent, or Firm* — Foley & Lardner LLP

(57) ABSTRACT

A device includes a pulse generator coupled to a neurostimulation lead placed around the nerve and a set of electrodes individually connected to the generator by a splitter circuit controlled to preferentially stimulate certain regions of the nerve relative to other regions. The device performing an iterative search of an optimal configuration operating by selection of a plurality of different stimulation configurations, storing of a cardiac physiological parameter measured for each selected stimulation configuration, and designation as optimal stimulation configuration of the one of said selected different stimulation configurations, depending on at least the stored values of the physiological parameter measured for different electrode configurations.

6 Claims, 6 Drawing Sheets

(52) U.S. Cl.
CPC ........ *A61N1/36114* (2013.01); *A61N 1/36125* (2013.01); *A61N 1/36185* (2013.01); *A61N 1/0551* (2013.01)

(56) References Cited

U.S. PATENT DOCUMENTS

| | | |
|---|---|---|
| 2011/0301658 A1 | 12/2011 | Yoo et al. |
| 2012/0065699 A1 | 3/2012 | Bedenbaugh |
| 2012/0065702 A1 | 3/2012 | Arcot-Krishnamurthy et al. |
| 2012/0239109 A1 | 9/2012 | Lee |
| 2012/0330369 A1 | 12/2012 | Osorio et al. |
| 2013/0103106 A1* | 4/2013 | Schotzko et al. ............ 607/2 |
| 2013/0165994 A1 | 6/2013 | Ternes et al. |
| 2013/0165998 A1* | 6/2013 | Libbus et al. ............ 607/62 |
| 2014/0005739 A1 | 1/2014 | Xi et al. |

FOREIGN PATENT DOCUMENTS

| | | |
|---|---|---|
| WO | WO-2006/027473 | 3/2006 |
| WO | WO-2009/020639 | 2/2009 |
| WO | WO-2009/025817 | 2/2009 |
| WO | WO-2011/040842 | 4/2011 |

OTHER PUBLICATIONS

Preliminary Search Report for French Patent Application No. 1454450, dated Jan. 8, 2015, 1 page.

The Johns Hopkins University Applied Physics Laboratory LLC, Electrode Array to Determine Specific Axonal Firing in a Peripheral Nerve, Reference #P02216, available at least as early as May 19, 2014, 1 page.

Tyler et al., Functionally Selective Peripheral Nerve Stimulation With a Flat Interface Nerve Electrode, IEEE Transactions on Neural Systems and Rehabilitation Engineering, vol. 10, No. 4, Dec. 2002, 10 pages.

* cited by examiner

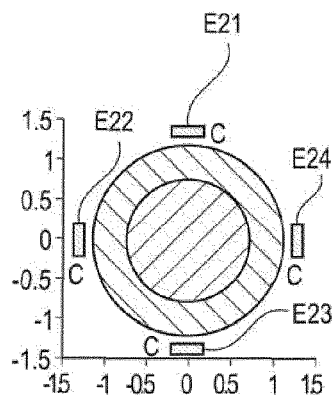
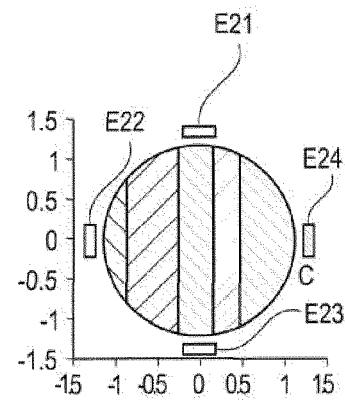
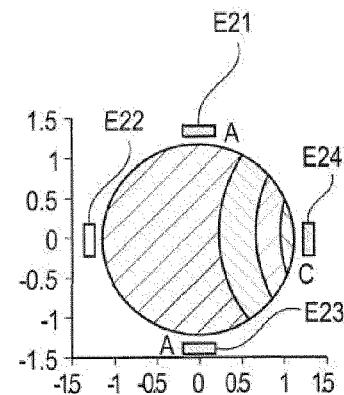
Fig. 4a     Fig. 4b     Fig. 4c
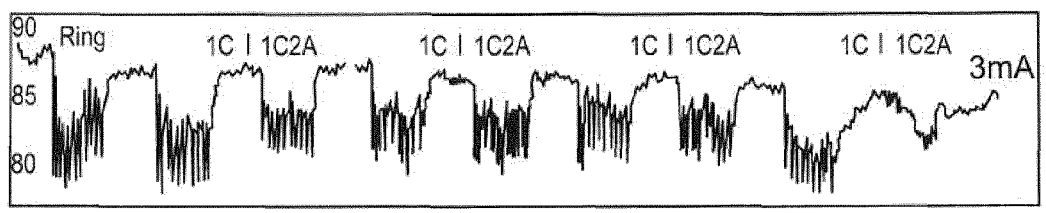
Fig. 5a
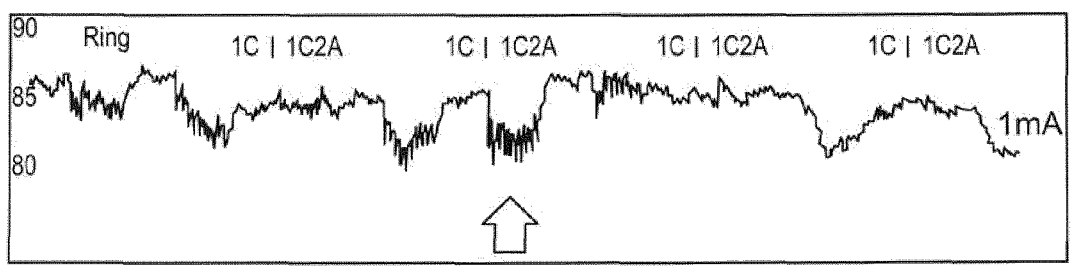
Fig. 5b

ACTIVE IMPLANTABLE MEDICAL DEVICE WITH AUTOMATIC OPTIMIZATION OF THE CONFIGURATION OF A MULTI-ELECTRODE STIMULATION LEAD

CROSS REFERENCE TO RELATED APPLICATIONS

This application claims the benefit of and priority to French Patent Application No. 1454450, filed May 19, 2014, which is hereby incorporated by reference herein in its entirety.

BACKGROUND

The present invention relates generally to nervous stimulation implantable devices. It relates more particularly, but is not limited to, an implant for delivering vagus nerve stimulation therapies, called VNS (Vagus Nerve Stimulation) therapies.

A nerve has many axons that innervate various organs and muscles of the human body. Some of these axons innervate the organ, muscle or structure intended to be subjected to therapy, whereas others innervate organs, muscles or structures which are not affected by the therapy.

Thus an overall, undifferentiated stimulation of a nerve may, beyond the desired therapeutic effect, induce undesirable effects in other organs, muscles or sensory feedback. Moreover, to have the desired therapeutic effect via the concerned axons, a non-differentiated excitation of all nerve fibers may require a much higher electric current than is necessary for the sought therapeutic effect.

It is consequently important to deliver a spatially selective stimulation of the target organ (typically, but not limited to, a nerve such as the vagus nerve) to achieve a focused effect on targeted physiological parameters while limiting side effects on non-targeted organs or muscles and while limiting the electrical current required for stimulation.

The therapy may be delivered according to various methods—all included in the scope of the present invention—by a neurostimulation lead disposed around, near or within the targeted structure. In the most common case, the lead consists of a cuff wrapped around a nerve, such as the vagus nerve. This cuff is provided with a plurality of electrodes which are applied against the inner surface of the nerve to selectively stimulate some regions thereof, by a controlled distribution of the currents applied to the various electrodes.

The following description will mainly refer to this mode of delivery of nerve stimulation therapy, but it is understood that it does not present a limitation. The invention is applicable as well to other types of leads, including tubular, stent-shaped leads introduced inside a vessel, for example the aorta, to stimulate some baroreceptor sites that have an indirect effect on the nervous system, or implanted leads directly inside the organ, typically a nerve or brain, for direct, in situ, stimulation of the nervous system.

A number of attempts to perform an advanced stimulation, or for particular applications, of certain nerve fibers have been described. In particular:
US 2012/065702 A1 describes a stimulation device with multiple electrodes for multiple stimulation, with priority management in function of the motor response;
WO 2009/025817 A2 and WO 2009/020639 A1 disclose a stimulator capable of assessing the response of a patient to various possible stimulation electrode configurations, including intracardiac electrodes, based on various criteria evaluated from physiological signals collected by sensors to determine the configuration providing the best therapy;
US 2014/0005739 A1 describes a neurostimulator capable of assessing the response of a patient to various possible electrode configurations, on the basis of an analysis of the patient's heart rhythm;
The article of Ordelman et al. "Selectivity for Specific Cardiovascular Effects of Vagal Nerve Stimulation With a Multi-Contact Electrode Cuff," *IEEE Transactions on Neural Systems and Rehabilitation Engineering*, Vol. 21, No. 1, January 2013, teaches the application of a bipolar stimulation with several pairs of contacts on a channel electrode;
WO 2011/040842 A1 discloses a cardiac stimulation device in which a series of stimulation electrodes are powered by respective conductors. A pulse generator applies pulses to different pairs of electrodes so as to perform stimulation according to several modes;
The notice #P02216 published by the Johns Hopkins University Applied Physics Laboratory, entitled "Electrode Array to Determine Specific Axonal Firing in a Peripheral Nerve" aims at identifying the fiber to stimulate by examining the response signals of the different fibers;
The article from Tyler and Durand "Functionally Selective Peripheral Nerve Stimulation With a Flat Interface Nerve Electrode," *IEEE Transactions on Neural Systems and Rehabilitation Engineering*, Vol. 10, No. 4, December 2002, offers a new electrode geometry for selective stimulation;
WO 2004/103455 A and WO 03/099377 A teach a unidirectional stimulation with a multipolar electrode for a cardiac application, so as to neutralize some induced effects;
US 2011/0301658 A tests different stimulation parameters and different positions of electrodes to identify certain nerve fibers during the surgical phase; it does not address an implantable autonomous stimulation device;
US 2012/0239109 A1 describes a quadripolar configuration of anodes for epidural stimulation for the treatment of pain;
US 2012/0065699 A1 describes a DBS (Deep Brain Stimulation) lead having a plurality of independently powered stimulation electrodes, as well as collection electrodes. The purpose is to target a given area by adjusting the pacing configuration, particularly to reduce the device consumption while providing methods of collection of a local signal;
U.S. Pat. No. 7,483,747 B2 discloses a nerve stimulation system with optimized consumption and the effectiveness of the implant, but by methods of stimulation profiles and parameters and not of electrode configurations;
US 2013/0165994 A1 describes a VNS lead with possibility of switching from one set of electrodes to the other to maintain the efficiency of the stimulation to avoid habituation or by readjusting the targets after a displacement of the VNS lead.

However, none of these proposals allows an optimization of the electrode configuration of a neurostimulator that takes into account the following three aspects: i) Consumption of the implant, which must be controlled very strictly for not burdening the life of the implant; ii) Maximization of the physiological effect produced by the neurostimulation therapy; and iii) Minimization of undesirable side effects induced by stimulation of the nerve (e.g. cough triggering).

SUMMARY

One object of the invention is to fully automatically provide a search mode for an optimal stimulation configuration of a multi-electrode neurostimulation lead which simultaneously takes into account these three criteria.

By "stimulation configuration," it must be understood to include any configuration combining the following criteria: i) the fact that an electrode is or is not an active electrode (that is to say, crossed by or not by a stimulation current); ii) the anode or cathode polarity of each active electrode (that is to say the direction of the current through this electrode); and iii) the distribution between the different active electrodes of the current produced by the neurostimulation generator.

By application of various aspects of the present invention, an electrode configuration that optimally applies neurostimulation depending on the desired effect may thus be determined and fixed. To this end, the invention proposes an active implantable medical device for providing neurostimulation by controlled application of electrical pulses simultaneously in several points of an organ. The device preferably includes, in a manner described in US 2012/065702 A1 above: a control device provided with an electrical pulse generator; a neurostimulation VNS lead adapted for placement around, near or inside the organ having a plurality of electrodes individually connected to the control device; and methods for measuring a physiological parameter representative of the patient's cardiac activity. The control device includes a splitter circuit associated with the control device capable of varying the stimulation configuration to preferentially stimulate certain parts of the organ with respect to other regions. The stimulation configuration includes determining the active electrodes connected to the pulse generator, the anode and cathode polarity of the active electrodes, as well as possibly the distribution of the respective currents delivered to these active electrodes.

The device further includes iterative search methods for optimum stimulation, including: selection of a plurality of different stimulation configurations; storage of the measured physiological parameter for each selected stimulation configuration; and designation, as the optimum stimulation configuration, of one of the different selected stimulation configurations based on at least i) the stored values of the physiological parameter measured for different electrode configurations.

According to preferred embodiments, the device further includes methods for detecting adverse effects that might be generated by neurostimulation, the storage methods of the physiological parameter also being able to store for each selected pacing configuration an indicator of the possible occurrence of an adverse event. Furthermore, the optimal configuration is also designated according to: ii) the stored values of the indicator of possible occurrence of an adverse effect, and iii) the number of active electrodes used as cathodes with each selected pacing configuration.

According to various advantageous subsidiary characteristics:
The optimum configuration is designated based on the result of the comparison of the stored values of the measured physiological parameter with a predetermined target level;
The optimum configuration is also designated according to the stored values of the physiological parameter measured for different distributions of the respective currents delivered to the electrodes, for a same configuration of electrodes;
The iterative search methods of optimal stimulation configuration is also capable of varying at least one parameter of the pulses, including the current intensity of the pulse and/or the number of pulses of a pulse burst.

DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIGS. 5a and 5b show an electrocardiogram response according to different orientations of the configurations of electrodes of FIGS. 4b and 4c.

DETAILED DESCRIPTION

An exemplary embodiment of the device of the invention will now be described. Implantable stimulation devices are intended to achieve neurostimulation therapy (e.g. on the vagus nerve) to treat various symptoms or conditions such as heart failure. This neurostimulation is for example performed by application of electric pulses to the conductors terminating in electrodes disposed in a lead surrounding the nerve (this particular example being, as mentioned above, in no way restrictive of the invention).

The battery longevity of the implanted stimulation device depends on parameters set by the practitioner to achieve pacing in the duration, primarily the amplitude, the width and the pulse frequency as well as the duty cycle of these pulses.

Regarding its software aspects, the invention may be implemented by appropriate programming of the controlling software of a known VNS stimulator. Such a pacemaker includes a programmable microprocessor provided with circuits for shaping and delivering stimulation pulses to implantable electrodes. It is possible to transmit to it telemetry software that will be stored in memory and executed to implement the functions of the invention that will be described below. The adaptation of these devices to implement the novel functions of the invention is within the scope of a skilled-in-the-art person, and will not be described in detail.

Software methods are involved in the implementation of the invention, being executed by a microcontroller or a digital signal processor. For the sake of clarity, the various processing applied will be broken down and diagrammed by a number of different functional blocks in the form of interconnected circuits, however this representation is only illustrative, these circuits having common elements and in practice corresponding to a plurality of functions overall performed by a single software.

Figure 1:
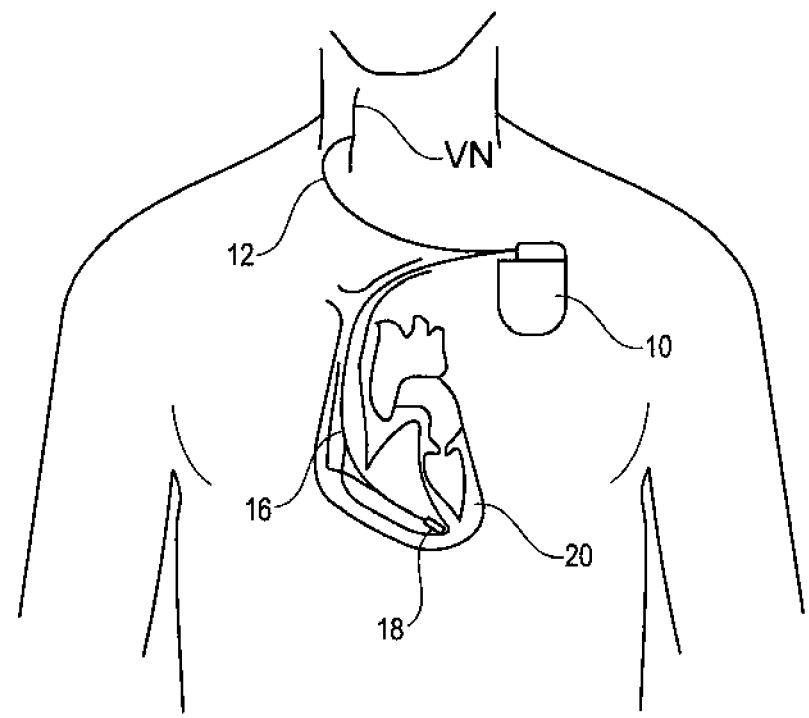
FIG. 1 is an overview presentation of the implantable device of the invention.

In FIG. 1, the reference 10 designates the implantable device for controlling vagus nerve stimulation. This stimulation is delivered by a lead 12 bearing at its distal portion 14 an arrangement of electrodes implanted around the vagus nerve VN and capable of selectively stimulating some fibers thereof by application of pulse bursts produced by the generator 10 on certain electrodes as discussed in detail below.

In a particular application to the control of cardiac activity, to allow the issuance of VNS pulse synchronous with the heartbeat, the generator 10 also has a cardiac lead 16 provided at its distal end of an electrode 18 collecting the electrical activity of the myocardium 20. This lead collects endocardial electrogram EGM signals that will drive the control device 10 so that it delivers to the vagus nerve 14 VNS stimulation pulses at the same rate as the heartbeat and at the most appropriate moment of the cardiac depolarization waves.

Figure 2:
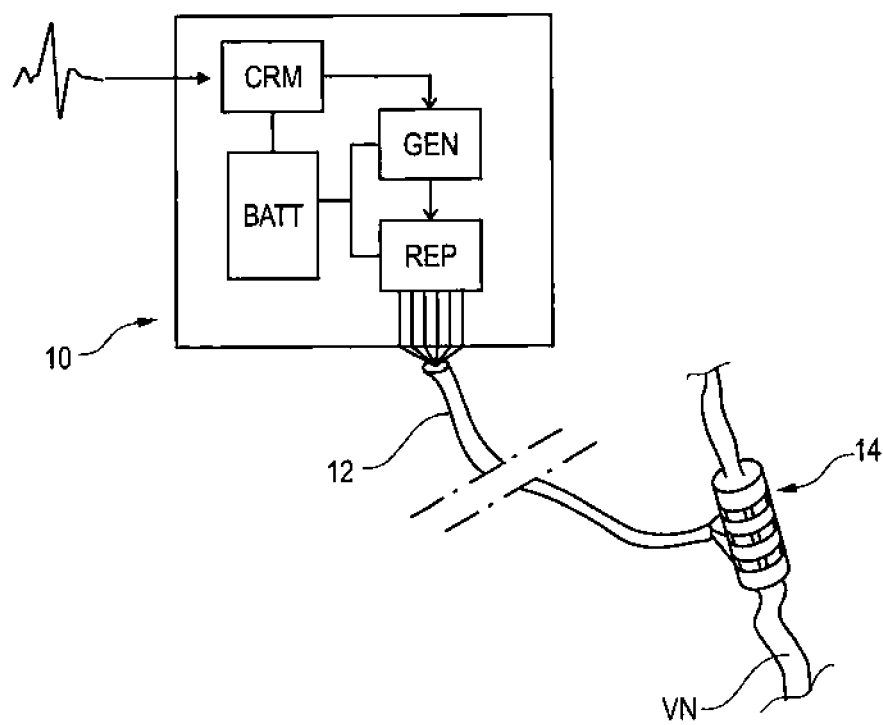
FIG. 2 is a more detailed view of a system (module control unit and neurostimulation lead) of the device of the invention.

FIG. 2 schematically shows the main features of the control device 10 of the invention device. This includes a generator circuit GEN able to produce pulse bursts of neurostimulation intended to be delivered to the vagus nerve via the lead 12. In the described cardiac application, the GEN circuit is controlled by a CRM circuit for management of the heart rate, receiving as input the EGM signal from the lead 16.

A first function of the CRM circuit is to drive the generator GEN so as to deliver neurostimulation pulse bursts, for example, in synchronism with the heartbeat, the latter being described and followed by markers corresponding to the instants of occurrence of the R-wave, representative of the peak of spontaneous depolarization of the ventricles.

The control device also includes a current distribution circuit REP for varying configurations of connections between the generator circuit GEN and the electrodes of the lead 12 of the vagus nerve, that is to say that the REP circuit is a circuit capable of i) defining each electrode of the lead 12 as a cathode, an anode, or an inactive electrode and ii) distributing the current produced by the generator between the individual anodes and cathodes so defined. Such a splitter circuit REP is described for example in WO 2006/027473 A1, which we can refer to for more details.

Figure 3A:
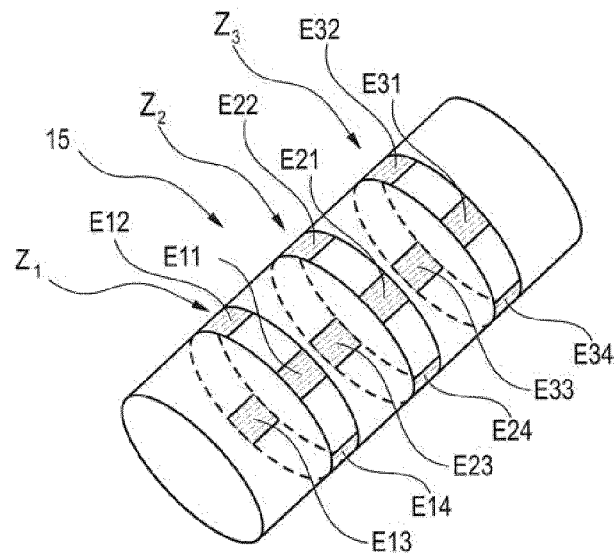
FIG. 3A is a perspective view illustrating an electrode arrangement for a preferred embodiment of the neurostimulation lead.

As shown in FIG. 3A, the electrodes of the lead 12 are preferably arranged in three annular zones Z1, Z2 and Z3 distributed in the longitudinal direction of the vagus nerve and carried by a cuff surrounding it. In a particular embodiment, all the electrodes occupy discrete angular sectors in the respective annular zones. For example, there are four electrodes in each annular zone, angularly spaced by 90° relative to the next. This number is not limiting. Typically, between 2 and 8 electrodes, regularly spaced or not, may be provided.

In the annular zones of ends Z1 and Z3, the electrodes are preferably all connected together to behave similarly, vis-à-vis the stimulation, a ring electrode in one piece. Alternatively, in the zones Z1 and Z3, a generally continuous annular electrode may be provided. In the central annular zone Z2, the four electrodes E21, E22, E23, E24 are selectivity electrodes individually connected to the pulse generator via the splitter circuit REP, in order for each electrode to be able to play the role of anode, or the role of cathode, or to be not connected (high impedance behavior).

Figure 3B:
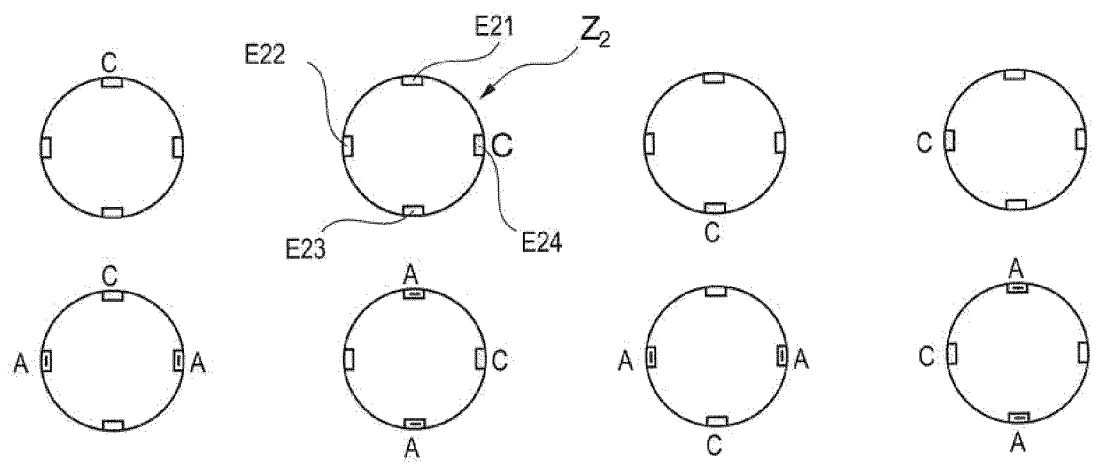
FIG. 3B illustrates a set of possible configurations for connections of the arrangement of electrodes of FIG. 3A, FIGS. 4a to 4c illustrate a modeling of the distribution of the electrical stimulation in the nerve section for three possible configurations of connections of electrodes of the lead.

Thus, FIG. 3B shows eight possible electrode configurations, wherein the four electrodes E21 to E24 of the intermediate zone Z2 are illustrated with an empty rectangle designating an unconnected electrode, while a full rectangle denotes a connected electrode either as an anode (letter A) or as a cathode (letter C). Shown are four configurations wherein one of the electrodes of the zone Z2 is connected as a cathode and the others are not connected, a configuration among them corresponding to a rotation of 90° to the previous one. It can also be observed four configurations wherein one of the electrodes is connected as cathode, the two adjacent connected as anodes, and the opposite electrode is not connected. Again, this configuration is repeated by successive rotations of 90°. Of course, any other combination of connections can be tested.

In the intended application intended to lowering the heart rate, electrodes of end regions Z1 and Z3 typically play the role of anodes, while the sector electrodes E21 to E24 of the intermediate zone Z2 may be unconnected (high impedance), connected as cathodes, or connected as anodes.

Naturally, the signal input of the device 10 is adapted so that the CRM control unit can examine the signal corresponding to the desired effect (here, for example, an electrocardiogram signal or a heart rate signal reprocessed from the electrocardiogram signal), and confront it with a target value ideally to be reached during a neurostimulation.

Referring now to FIGS. 4a to 4c, a simulation of the activation thresholds of the fibers with different electrode configurations is shown. Indeed, for that stimulation to be as selective as possible, it is necessary that the targeted fibers have the lowest possible activation threshold, and that non-target fibers have as high as possible an activation threshold.

The configuration of FIG. 4a corresponds to the case wherein the four electrodes E21 to E24 of the intermediate zone Z2 are all connected as cathodes, thus simulating the known case of a ring electrode. It is observed that the activation threshold of the fibers in the nerve section (different thresholds being represented by varying densities hatch) is not differentiated angularly, the threshold, however, being slightly lower in the periphery of the nerve than in its central area.

The configuration of FIG. 4b corresponds to the case wherein three electrodes in the zone Z2 are not connected, and the last on the right in FIG. 4b is connected as cathode C. It is observed in this case a minimum activation threshold in the vicinity of the cathode, and which gradually increases as one moves away horizontally from the cathode.

Finally, the configuration of FIG. 4c corresponds to the case wherein the electrode E24 on the right in the figure is connected as a cathode, while the two adjacent electrodes E21 and E23 (top and bottom) are connected as anodes, that is to say, both connected to the anode area Z1 and to the anode area Z3. It is observed that the low activation threshold area is narrower in the vicinity of the cathode, which allows greater selectivity in the section of the nerve subjected to stimulation, and therefore to more easily target nerve fibers that are to be stimulated while avoiding those that do not have to be. The current distribution in this last example is for example: 25% in one direction on each of the electrodes Z1, E21, E23 and Z3 (anodes), and 100% in the other direction on E24 (cathode).

Other distributions are possible with the same choice of cathodes/anodes, thus corresponding to different configurations within the scope of the invention, for example:
20% in one direction on Z1, 30% of E21, 25% on E23 and 25% on Z3 in the same direction (anodes), and 100% in the other direction on E24 (cathode), or
40% in one direction on Z1, 10% of E21, 10% on E23 and 40% on Z3 in the same direction (anodes), and 100% in the other direction on E24 (cathode), etc.

As discussed above with reference to FIG. 3B, the configurations of FIGS. 4b and 4c can be rotated of 90° to provide other configurations which in turn will enable to selectively stimulate other nerve fibers.

It is understood that other electrode configurations of the zone Z2 can also be tested, and in particular configurations with adjacent cathode and anode, opposed cathode and anode, a cathode and three anodes, etc. which allows for multiple combinations for each time preferentially stimulating an area of the nerve section having a certain contour. Furthermore, it is possible not only to act on the position of the anodes to differently focus the current, but also to implement a plurality of cathodes (typically two cathodes) in order to move the activation zone and thus aim fibers which would not be directly located under a cathode but rather between two cathodes.

It is also understood that by multiplying the number of sector electrodes in the annular zone Z2 (typically up to 8), the nerve region to be preferentially stimulated can be defined with better resolution. Furthermore, it should be noted that the zones Z1 and Z3 used as anodes in the embodiment above, may also be included in configurations with at least one anode and at least one unconnected electrode or an electrode connected as a cathode.

In this way, by varying the electrode configurations one can play finely on the distribution of currents in the nerve section, thereby achieving selectivity in the stimulation while reducing the power required for this stimulation, thereby increasing the battery lifespan.

Thus, an effect on a physiological parameter (in this case, a decrease in heart rate) can be obtained which is similar to that conventionally obtained with ring electrodes, but with a much more limited stimulation current and limiting the adverse impact the stimulation on other functions in which other fibers of the considered nerve are involved.

The present invention relates to a method for fully automatically determining the optimum configuration for a given patient. The CRM control module 10 is able to drive the splitter circuit REP for multiple pacing configurations are successively established while the device monitors a particular physiological signal reflecting the desired effect, in order to determine and store the optimal configuration and to freeze the switching circuit on the configuration for the operation for a certain duration of the implantable device.

It is also possible to repeat from time to time the configuration method during monitoring of the patient for determining and storing, as appropriate, an alternative configuration of electrodes, the effect of which is better, as also discussed in the following.

In an example shown in FIGS. 5a and 5b, changes in the heartbeat based on new electrode configurations were plotted, i.e. at the left of each illustration the configuration in FIG. 4a (denoted "RING" because the four electrodes around the nerve are all connected as a cathode), then the configurations of FIG. 4b (denoted "1C" for one cathode) and FIG. 4c (denoted "1C2a" for one cathode and two anodes), with the four different orientations as mentioned in the foregoing and shown in FIG. 3B.

It can be observed that for a 3 mA pulse intensity (FIG. 5a), one cannot identify a specific configuration which provides a reduction in heart rate which is substantially greater, in terms of amplitude and homogeneity, than other configurations. In addition, a current of 3 mA inevitably induces a decrease in the device autonomy and potential side effects, especially in a RING-type configuration wherein a large part of the nerve is stimulated.

However, as shown in FIG. 5b, for a pulse current of 1 mA, it is seen that for a certain configuration of the type "1C2a" (marked by arrow), a significant and consistent reduction in heart rate is obtained, while a standard RING-type configuration (on left of the figure) does not provide an effect anymore, with this level of pulse intensity. This particular configuration will then be fixed at the switch device controlled by the CRM control circuit methods for all the pulses, which in this example are determined based on signals received from the cardiac lead 16, are applied in this configuration.

Figure 6:
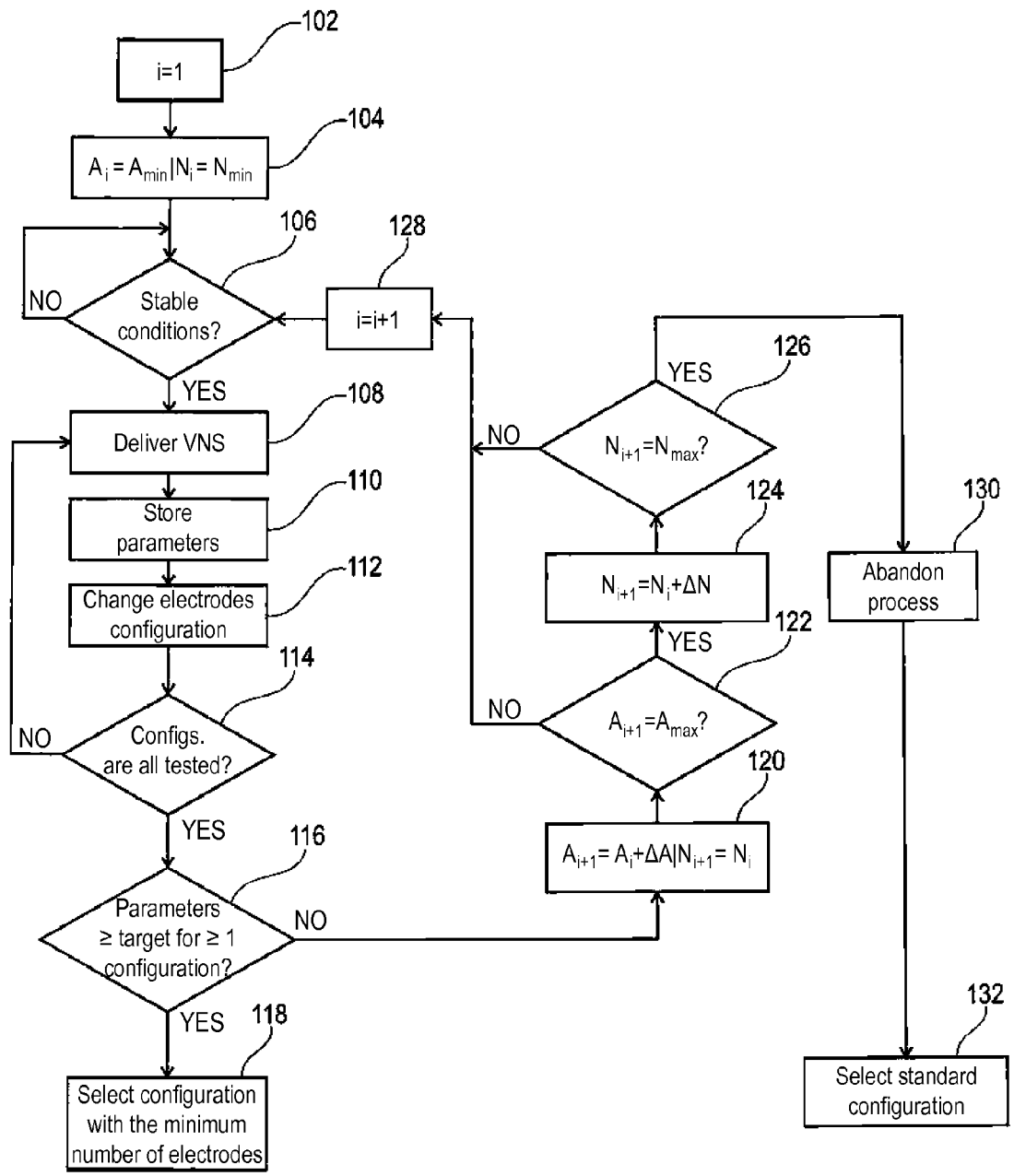
FIG. 6 is a flowchart illustrating the steps of a method for configuring an implantable neurostimulation device according to a first embodiment of the invention.

FIG. 6 is a flowchart illustrating the steps of a method of configuration of an implantable neurostimulation device according to a first embodiment of the invention. This method is the following:

One or more physiological parameters (such as the aforementioned electrocardiogram signal or a pressure signal in the left ventricle of the heart, or an endocardial acceleration signal) are recorded using known appropriate leads and acquisition systems. These signals are processed, also in known manner per se to reflect the effectiveness of the neurostimulation (typically for a percentage of increase in the RR interval giving the heart rate, a percentage of decrease of the cardiac contraction, etc.);

A first stimulation is programmed with minimal energy, a pulse amplitude $A_1=A_{min}$, and a minimum number of pulses $N_1=N_{min}$, the other parameters being constant; for example, $A_1$ and $N_1$ are fixed, $A_1=1$ mA and $N_1=1$ (blocks 102, 104), but these minimum values may be previously set to other values, by an initial configuration;

If the conditions of stability of the patient's condition are met (test of block 106), the stimulation as programmed is delivered to the nerve by the lead 12, 14 (block 108), and repeated as many times as there are electrode configurations to be tested (blocks 112 and 114) after storing of the measured physiological parameters (block 110) and changing of the configuration of the electrodes with appropriate programming of splitter circuit REP (block 112);

The configuration that ensures the best effect on the monitored targeted physiological parameter(s) is determined and selected by the system (blocks 116-118), for example by calculating the percentage of increase of the time interval RR (reflecting a corresponding decrease in heart rate). In case of configurations producing equivalent effect, the selected one is the one that, including the least number of cathodes, consumes less power;

If the calculated effect does not reach a preset target value, parameters such as the amplitude $A_i$ and/or the number $N_i$ of stimulation pulses are modified (blocks 120-128), and stimulation is repeated (blocks 110-114) on the different electrode configurations with these new parameters;

If, after trying all possible configurations, it is not possible to achieve the desired effect, then the method is stopped and basic standard configuration is selected by default (blocks 130 and 132).

In an implementation variant of this method, we can define a predetermined target (e.g., "10% reduction in heart rate") as being the optimum and stop scanning the different possible configurations of electrodes when the target effect is reached, without requiring testing of all possible configurations.

As noted above, this configuration method is implemented during implantation of the implantable neurostimulation device, but it can also be automatically repeated periodically to determine if any new configuration of electrodes is more effective. In fact, such phenomena as fibrosis, movement of the lead around the nerve, modification of the response of the nerve, etc., may lead to the fact that the configuration of electrodes previously determined is no longer the optimal configuration. A repetition of the method for determining the best configuration allows in this case finding and freezing, for a certain period until the next determination, the new optimal configuration.

Figure 7:
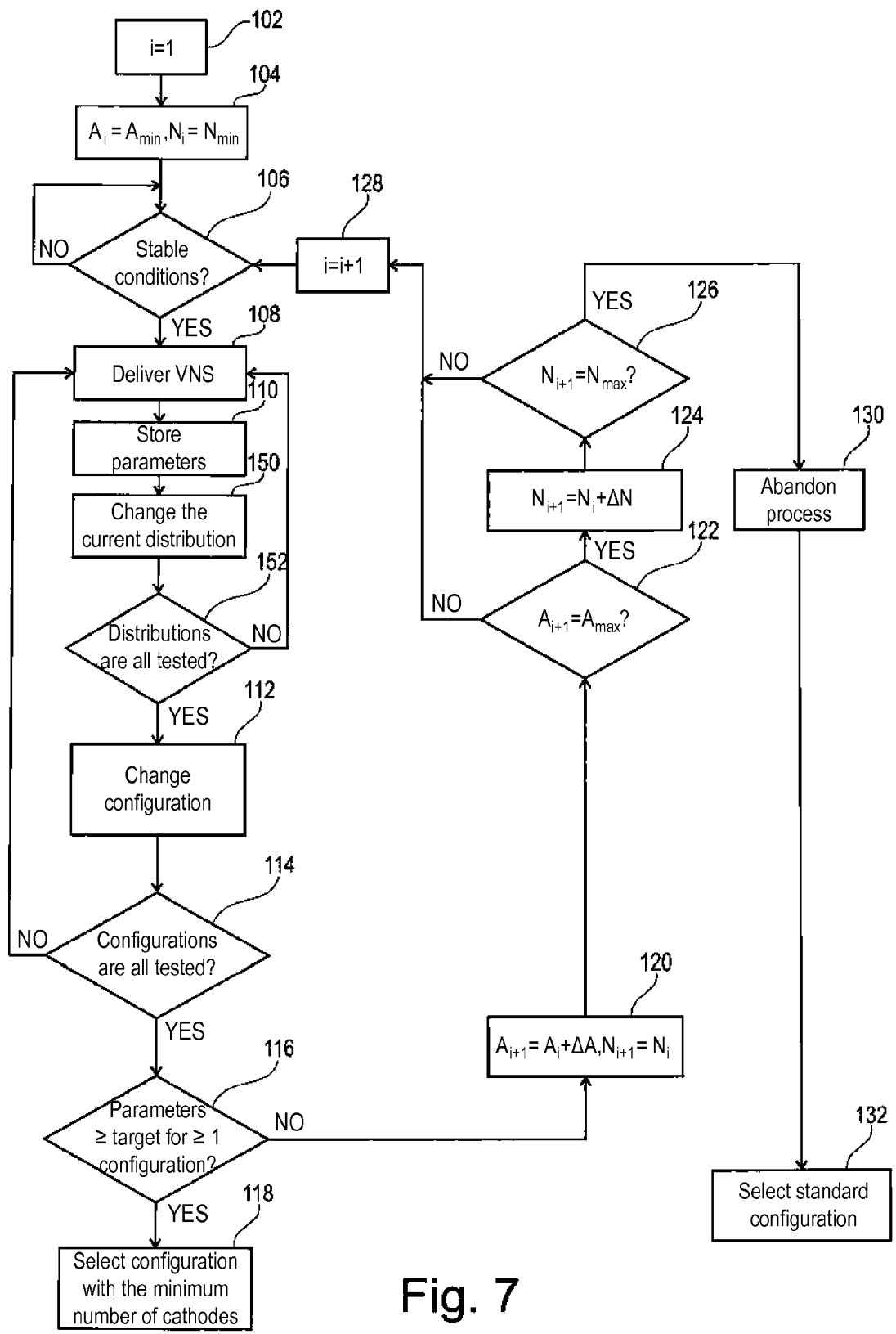
FIG. 7 is similar to FIG. 6 for a second embodiment of the invention.

FIG. 7 is a flowchart illustrating the steps of a configuration method according to a second embodiment of the invention. In this flowchart, the blocks 102-132 correspond to the same functions as those described above in connection with FIG. 6. The method differs in that it not only evaluates different electrode configurations (blocks 112 and 114), but it also evaluates, with a same electrode configuration, the impact of a change in the current distribution between the different electrodes (blocks 150 and 152). The selection of the best pacing configuration is thus performed based on a double choice: electrode configuration and current distribution.

Figure 8:
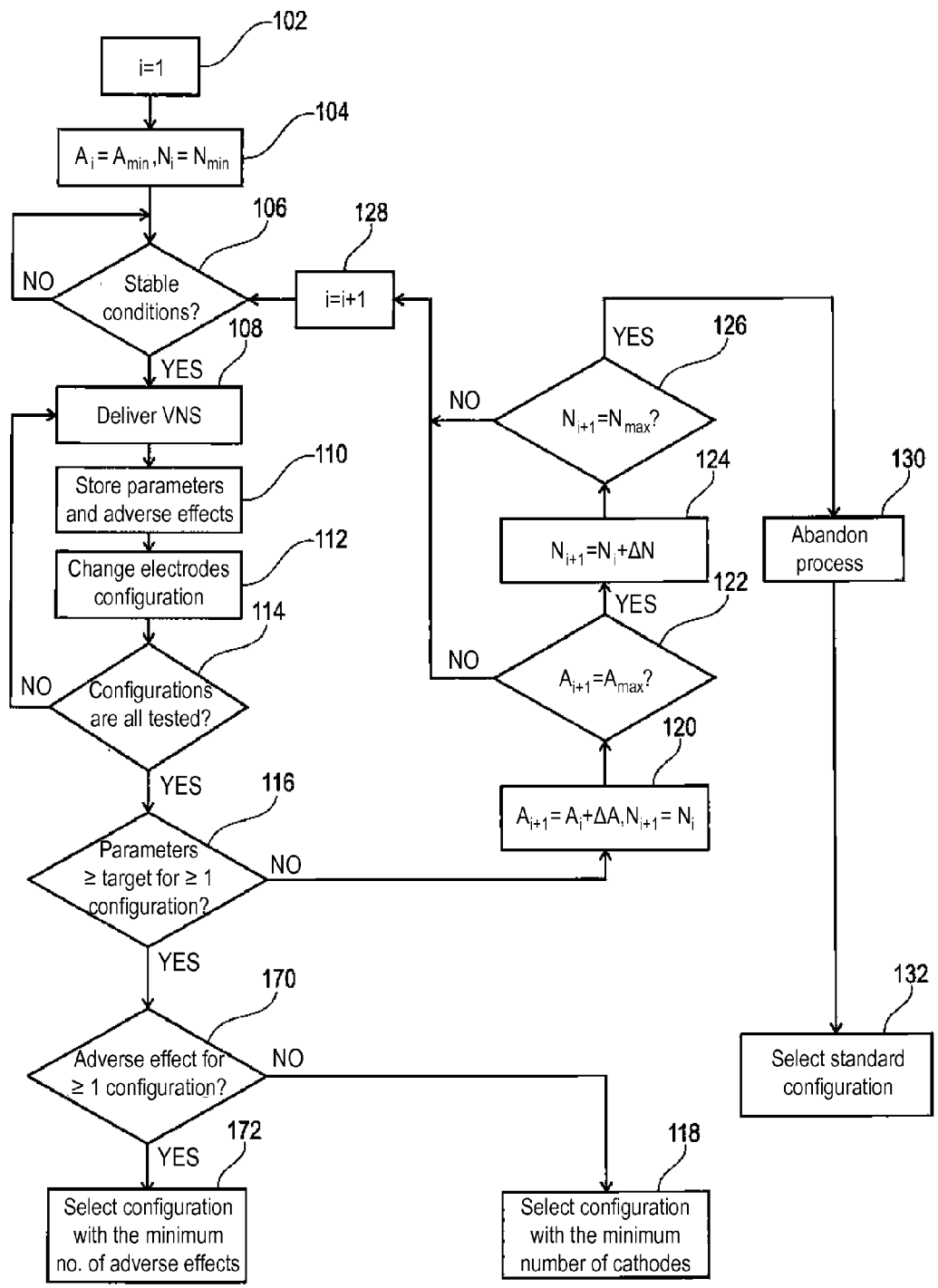
FIG. 8 is similar to FIG. 6 for a third embodiment of the invention.

FIG. 8 is a flowchart illustrating the steps of a configuration method according to a third embodiment of the invention. Again, the blocks 102-132 correspond to the same functions as those described above in connection with FIG. 6. The method differs in that it further detects, simultaneously with the measurement of the physiological parameter (block 110), the possible occurrence of adverse effects such as the onset of cough, detected for example by analyzing a minute-ventilation respiratory signal, or a signal from an accelerometer. Once all configurations are tested, the selected one will be in priority the one that produces the fewest adverse effects (blocks 170 and 172).

Of course, the present invention encompasses various variants and modifications within to the scope of the skilled person. In particular:

The number and arrangement of the electrodes can widely vary, depending especially on the desired fineness in terms of the stimulation selectivity;

The calculations to determine the best configuration of the electrodes with respect to the purpose can be made either by the computer embedded in the implantable device 10 or by an external computer appropriately interfaced with the device 10; and The "best electrode configuration" criteria can be determined very loosely based on different types of signals at different functions, able to reveal the effect of neurostimulation, whether on the vagus nerve or on other nerve fibers associated with different functions.

The invention is applicable not only in the field of cardiac stimulation and control, but also in other preventive or therapeutic functions such as DBS (Deep Brain Stimulation) and stimulation of the spinal cord, and more generally whenever a selective stimulation of a function with some nerve fibers is possible.

The invention claimed is:

1. An active implantable medical device of neurostimulation by controlled simultaneous application of electrical pulses in several points of a body, comprising:
    a control device with a generator of electrical pulses;
    a neurostimulation lead adapted to be placed around, near or within the body, and having a plurality of electrodes individually connected to the control device; and
    a sensing electrode for measuring a physiological parameter representative of the patient's cardiac activity, the physiological parameter being one of an electrocardiogram signal, a pressure signal in the left ventricle of the heart, and an endocardial acceleration signal,
    the control device having a distributor circuit associated with the control device and capable of varying the stimulation configuration to preferentially stimulate certain parts of the body with respect to other regions,
    said stimulation configuration comprising the selection of the active electrodes connected to the pulse generator, the anode or cathode polarity of these active electrodes, as well as the optional division of the respective currents delivered to these active electrodes,
    wherein the control device further comprises circuitry configured for iterative determination of an optimum stimulation configuration, wherein the iterative determination comprises:
        applying a plurality of different stimulation configurations;
        storing the measured physiological parameter for each applied stimulation configuration; and
        designating, as the optimum stimulation configuration, one of said selected different stimulation configurations, depending at least on the stored values of the physiological parameter measured for different electrode configurations;
    wherein the control device further comprises circuitry for detecting adverse effects that might be generated by neurostimulation, wherein storing the measured physiological parameter for each selected stimulation configuration comprises storing for each selected stimulation configuration an indicator of the possible occurrence of an adverse effect; and
    wherein the optimum configuration is also designated according to the stored values of the indicator of possible occurrence of an adverse effect and the number of active electrodes used as cathodes with each selected pacing configuration.

2. The device of claim 1, wherein the optimum configuration is designated based on the result of the comparison of the stored values of the measured physiological parameter with a predetermined target level.

3. The device of claim 1, wherein the optimum configuration is also designated according to the stored values of the physiological parameter measured for different distributions of the respective currents delivered to the electrodes, for a same configuration of electrodes.

4. The device of claim 1, wherein the iterative determination of an optimum stimulation configuration further comprises varying at least one parameter of the pulses.

5. The device of claim 4, wherein said parameter of the pulses is one of the intensity of the current pulse and the number of pulses of a pulse burst.

6. The device of claim 1, wherein designating, as the optimum stimulation configuration, further comprises calculating a percentage of increase in an RR interval descriptive of the heart rate or a percentage of decrease of cardiac contraction.

* * * * *